United States Patent [19]

Don Michel

[11] Patent Number: 5,306,249

[45] Date of Patent: *Apr. 26, 1994

[54] METHOD OF TREATING BODY PASSAGE WALLS

[76] Inventor: T. Anthony Don Michel, 309 Panorama Dr., Bakersfield, Calif. 93305

[ * ] Notice: The portion of the term of this patent subsequent to Jun. 29, 2010 has been disclaimed.

[21] Appl. No.: 868,961

[22] Filed: Apr. 19, 1992

Related U.S. Application Data

[60] Continuation-in-part of Ser. No. 808,924, Dec. 18, 1991, Pat. No. 5,222,941, which is a division of Ser. No. 492,582, Mar. 13, 1990, Pat. No. 5,090,960, which is a continuation-in-part of Ser. No. 464,029, Jan. 12, 1990, abandoned.

[51] Int. Cl.$^5$ ............................................. A61M 29/00
[52] U.S. Cl. ........................................ 604/101; 128/898; 128/632; 606/194; 604/28
[58] Field of Search ........................... 604/96–101, 604/49; 128/632, 898; 606/191, 192, 194

[56] References Cited

U.S. PATENT DOCUMENTS

| | | | |
|---|---|---|---|
| 4,512,348 | 4/1985 | Uchigaki et al. | |
| 4,610,662 | 9/1986 | Weikl et al. | |
| 4,636,195 | 1/1987 | Wolinsky | 604/101 |
| 4,696,668 | 9/1987 | Wilcox | 604/101 |
| 4,705,503 | 11/1987 | Dorman et al. | |
| 4,976,692 | 12/1990 | Atad | 604/101 |
| 5,059,178 | 10/1991 | Ya | 604/101 |
| 5,078,735 | 1/1992 | Capioli | |
| 5,097,834 | 3/1992 | Skrabol | |
| 5,109,850 | 5/1992 | Blanco et al. | |
| 5,135,484 | 8/1992 | Wright | 604/101 |
| 5,222,941 | 6/1993 | Dan Michael | 604/101 |

Primary Examiner—C. Fred Rosenbaum
Assistant Examiner—Chalin Smith
Attorney, Agent, or Firm—Spensley Horn Jubas & Lubitz

[57] ABSTRACT

A method for performing a therapeutic treatment on a section of a wall of a body passage, by: isolating a portion of the body passage which encloses the section from the remainder of the body passage; introducing into the isolated portion of the body passage a liquid medium containing a treatment agent; maintaining the treatment agent in the isolated portion for a predetermined time period; during the step of maintaining, periodically withdrawing a sample of the liquid medium from the isolated portion of the body passage, analyzing the sample to determine the proportion of treatment agent present in the liquid medium in the isolated portion and modifying the liquid medium in the isolated portion to establish a desired proportion of the treatment agent in the liquid medium in the isolated portion.

7 Claims, 3 Drawing Sheets

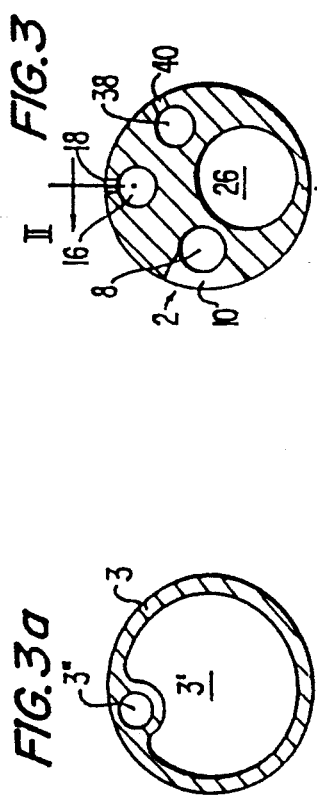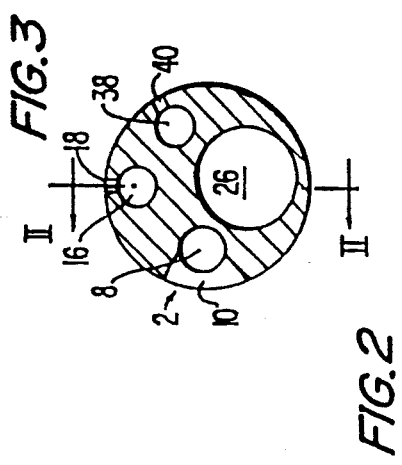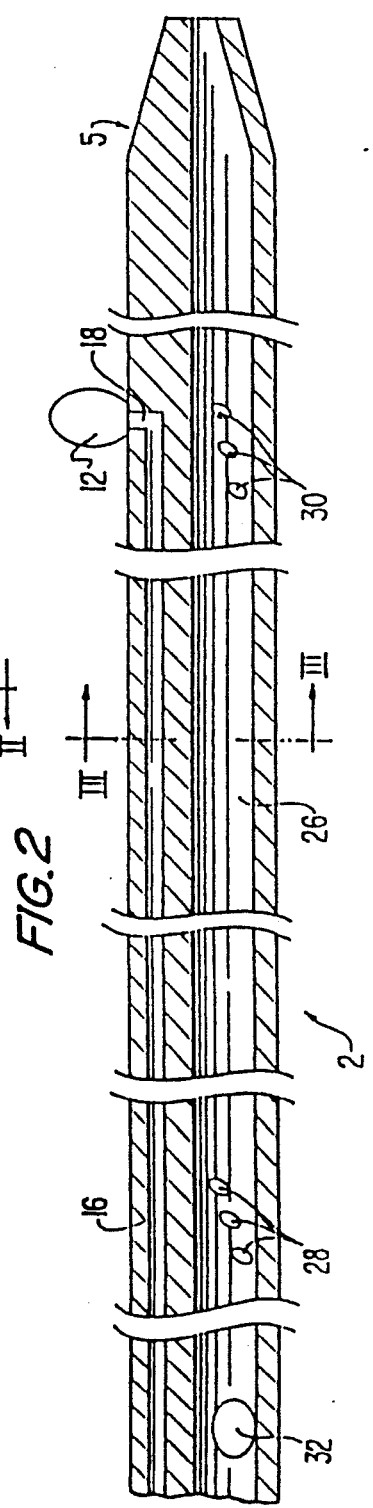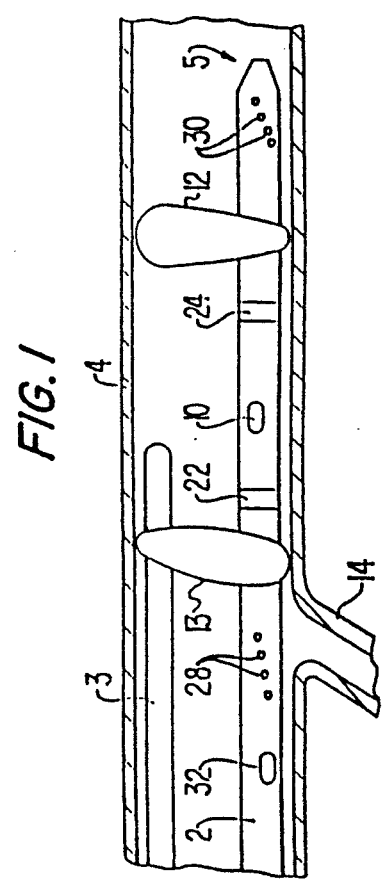

METHOD OF TREATING BODY PASSAGE WALLS

CROSS REFERENCE TO RELATED APPLICATIONS

This is a continuation-in-part of application Ser. No. 07/808,924, filed Dec. 18, 1991, now U.S. Pat. No. 5,222,94 division of application Ser. No. 07/492,582 filed Mar. 13, 1990, now U.S. Pat. No. 5,090,960 itself a continuation-in-part of application Ser. No. 07/464,029 filed Jan. 12, 1990, now abandoned.

BACKGROUND OF THE INVENTION

The present invention relates to the therapeutic treatments of blood vessels and possibly other body passages, and particularly treatments in which a chemical agent, antibodies, other biological material, or modified cells are brought into contact with, or implanted in, the wall of a body passage in order to reverse or prevent a pathogenic condition.

Medical research has led to the discovery of a number of treatments of this type which may be developed into clinically useful procedures. Examples of such treatments are described in Nabel et al, Recombinant Gene Expression in Vivo Within Endothelial Cells of the Arterial Wall, SCIENCE, Vol. 244, Jun. 16, 1989, pages 1342-4.

However, clinical application of such treatments requires a procedure which can be performed in vivo without giving rise to any unacceptable side effects.

In the case of blood vessels, this generally means that the material to be applied to the vessel walls must be confined to the treatment site. Otherwise, it would be necessary to introduce a large quantity of treatment material into the vascular system, with the attendant danger of harmful side effects.

A second requirement which exists in the case of treatment of blood vessels is that a sufficient flow of blood be maintained past the treatment site, particularly if the treatment requires a prolonged period of exposure of the vessel wall to the treatment material.

Finally, it appears that many treatments of the type here under consideration can be performed effectively or optimized only if the proportion of treating material in the fluid at the treatment site is maintained within a defined range.

U.S. Pat. No. 4,423,725, which issued to O. E. Baran on Jan. 3, 1984, describes an intervention device composed of a catheter having a blood flow lumen, a chemical delivery lumen and a suction lumen, associated with two annular cuffs which are inflatable to isolate a blood vessel region containing an obstruction. This patent discloses the treatment of blood vessel obstructions by balloon angioplasty followed by the application of anticoagulant drugs or cholesterol diluting drugs. A similar device for performing chemical dissolution treatments is disclosed in U.S. Pat. No. 4,610,662, which issued to Weikl et al on Sep. 9, 1986.

SUMMARY OF THE INVENTION

It is therefore an object of the present invention to perform such treatments in a minimum of time and while introducing a minimum of dissolution agent into the blood vessel.

Another object of the invention is to effect such treatments by a simple and readily controllable procedure which allows, particularly, control of the relative concentrations of treatment agent and blood or saline solution at the treatment site.

The above and other objects are achieved, according to the present invention, by a method for performing a therapeutic treatment on a section of a wall of a body passage, comprising: isolating a portion of the body passage which encloses the section from the remainder of the body passage; introducing into the isolated portion of the body passage a liquid medium containing a treatment agent; maintaining the treatment agent in the isolated portion for a predetermined time period; during the step of maintaining, periodically withdrawing a sample of the liquid medium from the isolated portion of the body passage, analyzing the sample to determine the proportion of treatment agent present in the liquid medium in the isolated portion and modifying the liquid medium in the isolated portion to establish a desired proportion of the treatment agent in the liquid medium in the isolated portion.

BRIEF DESCRIPTION OF THE DRAWINGS

FIG. 1 is a side view of a first embodiment of a device for performing treatments according to the present invention.

FIG. 2 is a side cross-sectional view of sections of the distal portion of one catheter of FIG. 1, to a larger scale, taken along line II—II of FIG. 3.

FIG. 3 is a transverse, or axial, cross-sectional view taken along the line III—III of FIG. 2.

FIG. 3a is a view similar to that of FIG. 3 showing the other catheter of FIG. 1.

DESCRIPTION OF THE PREFERRED EMBODIMENTS

Figure 5:
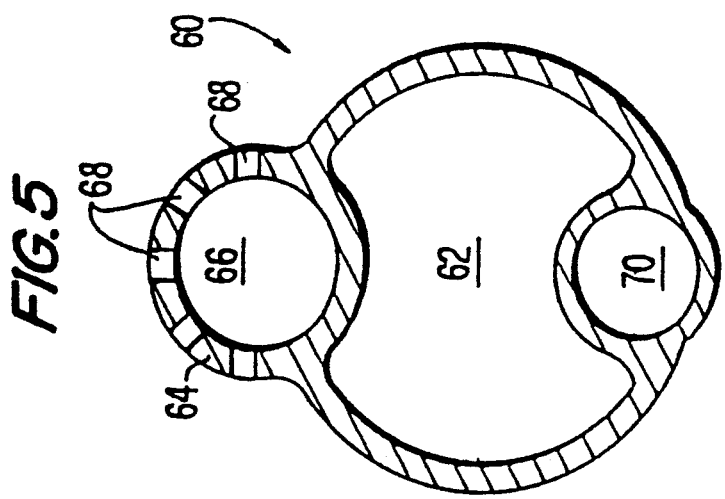
FIG. 5 is a side view, partly in cross section, of a third embodiment of the one catheter of FIG. 1.

The method according to the invention may be beneficially employed to introduce modified cells, i.e. cells which have been altered or treated, into blood vessel walls to achieve a variety of therapeutic results. By way of example, vascular endothelial cells may be genetically altered in a manner to transmit recombinant DNA products that may provide anticoagulant, vasodilatory, angiogenic, or growth factors to a localized segment of a blood vessel. Them, the altered cells are introduced into the blood vessel to be treated and are confined to the localized segment for a time sufficient to permit attachment of at least some of the cells to the vessel wall. This method may be practiced with cells which have been treated with lysosomes, or by electroporation, or with retroviruses to cause them to undergo molecular or genetic configuration changes which enable them to have a particular effect on the vessel wall tissue.

According to the invention, a quantity of cells, after having been altered or treated, is suspended in a vehicle, i.e. a saline solution or blood, which is then introduced into the localized segment of the blood vessel. The cells must be maintained in contact with the vessel wall for a certain period of time, up to one hour for the types of treatments which are contemplated herein. This requires a flow of blood past the treatment site while the cells remain confined to the treatment region. One frequently significant factor in the success of such treatments is the concentration of cells in the fluid at the treatment site. In methods according to the invention, the composition of fluid at the treatment site is monitored at regular intervals to determine the relative proportion of cells. If the monitoring result shows that the cell concentration is lower than optimum, an additional quantity of cells will be added to the treatment region; if the concentration is higher than optimum, the relative proportion of vehicle is increased. The composition of the fluid at the treatment site may be varied as follows:

after an initial mixture of modified cells and vehicle is introduced to the treatment site, a sample is withdrawn from the fluid periodically and is measured;

depending on the result of each sample measurement, the fluid withdrawn during the sampling step is replenished with fluid having a greater or lesser proportion of modified cells.

If fluid is gradually lost from the treatment site, it will most likely be replaced by blood. Therefore, sampling will reveal a decrease in modified cell concentration, which can be corrected by addition of a higher proportion of modified cells.

Other treatments according to the invention can involve the application of antibodies or other biological material to the vessel or body passage wall.

The invention can also be employed to bring chemical agents, antibodies, viruses, bacteria, or other biological materials into contact with a vessel or body passage wall.

A primary advantage of the invention is that it allows the treatment agent concentration to be accurately controlled during a prolonged treatment period. Given the small volume of the region containing the treatment agent solution or suspension, this is of great importance to the success of the treatment; if the concentration is too high, a destructive result can occur, while if the concentration is too low, the treatment result can be insufficient.

The results which can be achieved by treatments according to the invention include formation of a therapeutic coating on the vessel wall and destruction of tumors.

In order to perform a treatment according to the invention, it is necessary to bring a suitable treatment agent into contact with the vessel or body passage wall. Referring to FIG. 1, in order to deliver such agent to the site, catheter 2 is provided with an axial lumen 8 (FIG. 3) whose distal end terminates in a comparatively large outlet opening 10. The proximal end of lumen 8 (not shown) would extend outside of the patient's body and be connected to a suitable source of the treatment agent, or a mixture of the treatment agent and a saline solution.

Good medical practice generally dictates that the quantity of any foreign substance introduced into a patient's body be no more than that required to produce the intended result, whereby side effects can be prevented or at least minimized. In order to minimize the quantity of treatment agent employed to produce the desired result, the illustrated device will serve to block the blood vessel at a location downstream of the treatment site so that the agent introduced via lumen 8 and outlet opening 10 Will be confined to the region of the treatment site. Since the agent will be substantially prevented from flowing away from the treatment site, it will be appreciated that this arrangement allows the quantity of substance introduced into the body to be maintained at the minimum amount needed to produce the desired result.

The speed of the treatment action is influenced by the quantitative relation between the treatment agent and the blood or saline solution with which the treatment agent is mixed and a given reaction will be optimized by maintaining this relation in a given range. According to this invention, optimization can be achieved by controlling the flow rate of agent to the treatment site, controlling the quantity of blood or saline solution at the treatment site, and monitoring the resulting chemical composition at the treatment site. The proportion of agent at the treatment site is further controlled to prevent or minimize injury to the blood vessel wall.

FIG. 1 shows the distal end portion of a treatment device composed of, in addition to, infusion catheter 2, a suction catheter 3 in position in a blood vessel 4. Catheter 2 may be tapered at its distal end 5 to facilitate insertion and advance to the treatment site.

Catheter 2 is provided with a plurality of lumens and lateral openings which perform various functions in a treatment procedure. The internal structure of catheter 2 is illustrated more fully in FIGS. 2 and 3, to which reference will now be made together with FIG. 1.

Because a separate catheter 3 is employed to perform the suction operation, the suction lumen in catheter 3 can be made larger than a suction lumen which might otherwise be provided in catheter 2.

According to one embodiment of the present invention, the treatment site in vessel 4 may be blocked by a balloon 12 fixed to the peripheral wall of catheter 2 and a balloon 13 fixed to the peripheral wall of catheter 3, each balloon having an inflation opening for the introduction of inflation air via a lumen and an outlet opening of its respective catheter. In FIG. 2, a lumen 16 and outlet opening 18 for balloon 12 are shown. Balloons 12 and 13 are shown in their inflated state in FIG. 1 and balloon 12 is shown in its deflated state in FIG. 2.

As is apparent from FIGS. 1 and 2, balloons are constructed such that the inflation opening of each balloon is attached to a small portion of the periphery of the associated catheter and each balloon expands eccentrically relative to the longitudinal axis of its catheter. This is particularly desirable with regard to catheter 2, which is normally inserted first, because expansion of balloon 12 will urge catheter 2 toward the wall of vessel 4 leaving a relatively large free space for insertion of catheter 3. On the other hand, balloon 13 may be eccentric, as shown, or concentric, i.e., in the form of an annular cuff.

While embodiments are conceivable in which both balloons 12 and 13 are carried by catheter 2, in which case inflation of balloon 13 would be effected via a separate lumen and outlet opening, the mounting of balloon 13 on catheter 3 offers the advantage of permitting variation of the length of the blood vessel region enclosed by the balloons.

In the case where the treatment site is close to a branching blood vessel, as shown at 14 in FIG. 1, balloon 13 can be positioned to isolate the branching vessel from the treatment site. However, it may be necessary to insert a separate balloon catheter into the branching vessel in order to block flow in that vessel.

As an alternative to a balloon, or balloons, any other known devices can be employed to obstruct blood flow downstream of the treatment site, such devices including, for example, filters or sponges. Such devices should be constructed, however, to urge catheter 2 toward the wall of vessel 4. Preferably, a sponge would be provided in place of the balloon which is located upstream with respect to the direction of blood flow.

The peripheral wall of catheter 2 is provided with two radiopaque markers 22 and 24 which are spaced apart by a distance sufficient to straddle the treatment site and these markers could, for example, be in the form of annular bands. Passage 10 is located essentially midway between markers 22 and 24 and balloon 12 is located between distal marker 24 and distal end 5.

When catheter 2 is properly positioned at the treatment site and balloons 12 and/or 13 are inflated so as to block blood flow in vessel 4, it is desired to maintain a flow of blood past the treatment site and this is achieved, according to the present invention, by providing catheter 2 with a further lumen 26 having associated inlet openings 28 and outlet openings 30. Preferably, lumen 26 is given as large a diameter as is permitted by the available cross section of catheter 2 and the number of inlet openings 28 and outlet openings 30 is selected to provide a sufficiently low flow resistance. At the outlet end, lumen 26 extends completely to distal end 5 of catheter 2 and will serve the additional function of accommodating a guide wire during insertion of the catheter, as will be described below. However, particularly if end 5 is tapered, the outlet end of lumen 26 could present an unacceptably high flow resistance. Outlet openings 30 overcome this difficulty.

As is illustrated, openings 28 and 30 are located so that blood flowing through lumen 26 will bypass balloon 12, as well as the treatment site, when catheter 2 is properly positioned. By way of example, the spacing between openings 28 and radiopaque marker 22 could be of the order of 4 cm. Balloon 13 will be positioned so that openings 28 will always be located to be more remote from the distal end of the catheter than is balloon 13.

Lumen 26 is further associated with a dye outlet opening 32 which is located upstream of openings 28 and via which a suitable radiopaque dye may be delivered to the treatment site in order to assist X-ray observation of the positioning of catheter 2. By making opening 32 sufficiently large, dye delivered via the proximal end of lumen 26 will flow essentially entirely through opening 32, both because that opening will present a substantially lower flow resistance than will the downstream portion of lumen 26, and because the dye will be entrained in blood flowing through the vessel around catheter 2. During this time, balloon 12 is not yet inflated and either catheter 3 is not yet inserted or its balloon 13 is not inflated.

If catheter 2 is intended to be inserted into a vessel in the direction counter to blood flow, dye could be delivered via a further lumen (not shown) having outlet opening 32 disposed between distal end 5 and outlet opening 10, or a separate dye-delivery catheter could be employed.

The injection of dye or other observable agent, together with observation of its behavior in the blood vessel, allows the positioning of catheters 2 and 3 and the appropriate inflation states of balloons 12 and 13 to be determined. For example, if the dye flows off via a side branch, such as branch 14 in FIG. 1, catheter 13 may have to be displaced or a separate balloon may be required in the side branch. The direction of flow of the dye can indicate which balloon will have to be deflated to admit additional blood to the treatment site. If the dye remains in place, it may be possible to perform the treatment without inflating the balloons.

FIG. 3 shows, in axial cross section, one suitable arrangement of lumens in catheter 2. These can include a lumen 38 and an outlet opening 40 for delivering inflation air to balloon 13 if that balloon is carried by catheter 2. Similarly, FIG. 3a shows catheter 3 having a large area suction lumen 3' and a balloon inflation lumen 3''.

A treatment operation according to the present invention could be carried out by the following procedure, which incorporates conventional insertion techniques. The procedure to be described by way of example is intended to effectuate a treatment in a coronary artery, and consists of the following sequence of steps:

1) A needle is inserted into the artery from outside the body, one location currently used being in the patient's groin.

2) A guide wire is inserted through the needle and into the artery to a distance possibly of the order of 10 cm.

3) The needle is then removed.

4) A sheath is slid around the guide wire and into the artery.

5) A guiding catheter is placed around the guide wire and into the sheath, the guiding catheter is advanced into the coronary artery, and the sheath is removed form the artery.

6) The guide wire is then advanced through the guiding catheter and then past the distal end of the guiding catheter and across the treatment site.

7) The guiding catheter is then withdrawn from the artery.

8) Then, infusion catheter 2 having the form shown in FIGS. 1-3 is placed over the guide wire, i.e., lumen 26 is threaded around the guide wire and catheter 2 is advanced to the treatment site, the position of catheter 2 being observable by the effect of X-rays on markers 22 and 24.

9) when it appears that catheter 2 is at least approximately correctly located, the guide wire may be withdrawn and a suitable dye is introduced via lumen 26 and opening 32 into the blood stream in order to allow X-ray observation of the treatment site and behavior of the dye and to permit final positioning of catheters 2 and 3.

10) When it is determined that catheter 2 has been properly positioned, eccentric balloon 12 is inflated in order to block one side of the region which is the treatment site and to urge catheter 2 to one side of the artery.

11) Suction catheter 3 is then inserted and advanced to the treatment site, if necessary by a procedure as outlined at 1)-8).

12) Balloons 12 and 13 will be inflated and treatment agent possibly in mixture in a saline solution, is introduced, via lumen 8 and opening 10, at a rate sufficient to establish a sufficient concentration thereof at the treatment site. Fluid is periodically withdrawn from the treatment site via catheter 3 and analyzed. If the concentration of treatment agent is low, the delivery rate thereof is increased, or the downstream balloon is inflated if it was previously deflated; if it is high, the delivery rate may be decreased and/or the upstream balloon is partially deflated to allow an additional quantity of blood to enter the treatment site. After a selected treatment period, suction is established to remove the treatment agent, if necessary, the balloons may are deflated and the catheters are withdrawn.

Thus, according to the invention, treatment agent may be confined to the region between balloons and is prevented from flowing off into the remainder of the circulatory system. This means that the treatment agent is prevented from reaching regions of the circulatory system which may, because of disease or abnormality, cause serious harm to the patient.

At the same time, the fluid composition at the treatment site can be fully controlled in the manner described above.

One side of the treatment site can be blocked by an eccentric balloon carried by the infusion catheter or by a separate balloon carried by the suction catheter. In the latter case, the balloon carried by the suction catheter can be moved relative to the balloon carried by the infusion catheter to adjust the length of the region blocked off by the balloons, and/or to close off a side branch adjacent the treatment site.

Certain treatments contemplated by the invention may require that the treatment site be free, or substantially free, of blood. To achieve this, the balloon or other devices bounding the treatment site are constructed to effect a substantially complete flow blocking action and between steps 11) and 12), above, all fluid is evacuated from the treatment site via suction catheter 3.

For the majority of applications, catheter 2 may have a size of the order of 4.5 to 7 French, a size of 5.5 French presently being preferred.

Figure 4:
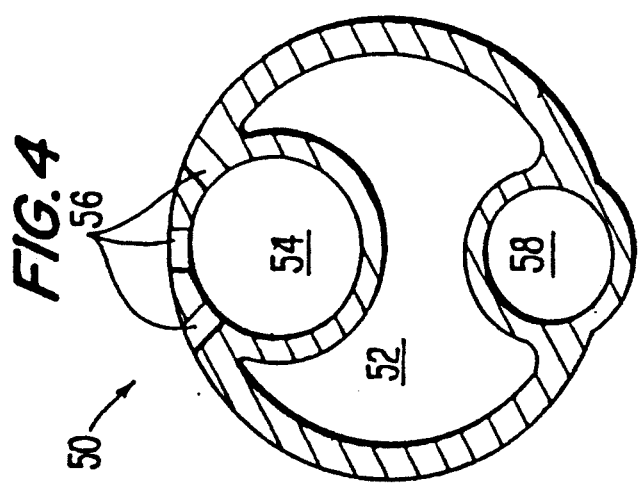
FIG. 4 is a side view, partly in cross section, of a second embodiment of the one catheter of FIG. 1.

Two further embodiments of a catheter for performing treatments according to the present invention are illustrated in cross section in FIGS. 4 and 5. Each of these embodiments, like the embodiment of FIGS. 1-3, may be a unitary, extruded plastic member, the embodiments of FIGS. 4 and 5 being constructed to have a thin-walled design in order to provide relatively large flow passages. In this connection, priority should be given to the cross-sectional area of the blood bypass flow path since the maximum possible flow rate along this path can prove beneficial to the patient.

FIG. 4 illustrates a catheter 50 having a basically cylindrical form and an internal configuration which provides a lumen 52 defining a blood bypass flow path occupying substantially more than one-half of the catheter interior cross section. Along the upper portion of catheter 50, there is provided a lumen 54 defining a treatment agent flow path which will communicate with the region surrounding catheter 50 via a plurality of outlet passages 56 which replace the single large opening 10 of the embodiment shown in FIGS. 1-3.

Finally, catheter 50 is provided with a balloon inflation lumen 58.

In this embodiment, the wall of lumen 58 projects radially slightly beyond the basic circular outline of catheter 50 in order to permit the cross-sectional area of lumen 52 to be enlarged.

In the embodiment shown in FIG. 5, catheter 60 is formed to have a still larger blood bypass flow lumen 62 by constructing the thin-walled structure of catheter 60 to have a radially protruding portion 64 which encloses a lumen 66 for delivering treatment agent. Because of the radially protruding position of portion 64, the outlet end of lumen 66 can be provided with a number of outlet openings 68. Catheter 60 is completed by a balloon inflation lumen 70 corresponding essentially to lumen 58 of FIG. 4.

In each of the embodiments illustrated in FIGS. 4 and 5, a second balloon inflation lumen may be provided at any desired location if the catheter is to carry the second balloon 13 which is to be separately inflated. In addition, the catheters according to these embodiments can have a tapered distal end, as shown for the embodiment of FIGS. 1-3, and lumens 52 and 62 will extend the entire length of the catheter to serve the additional function of accommodating a guide wire.

Further, in the embodiments of FIGS. 4 and 5, a radiopaque dye may be delivered to the region of the treatment site via the blood bypass flow lumen 52, 62, in a manner similar to that described above with reference to FIGS. 1-3. Specifically, lumen 52, 62 can extend fully to the proximal end of the catheter and, at a location upstream of the blood bypass flow region, this lumen may be provided with a large opening or an array of openings via which all or substantially all of a dye introduced via the proximal end of the catheter will exit into the blood stream. When no dye is being delivered, this opening or openings may serve as additional blood bypass flow inlet openings.

Figure 6:
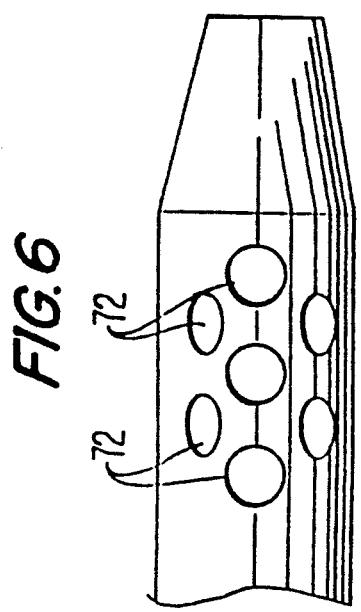
FIG. 6 is a side view of the distal end of an embodiment of the one catheter of FIG. 1.

In each embodiment of the present invention, the inlet and outlet openings for the blood bypass flow path may be constituted by an array of openings 72, as shown in FIG. 6. This array may be distributed around one-half of the circumference of the catheter or, in the embodiments of FIGS. 4 and 5, may be provided in both halves of the circumference of the catheter, outside of the regions occupied by the other lumens, 54, 58, 66, 70. Openings 56 and 68 may also be distributed to have the form of array 72.

Figure 7:
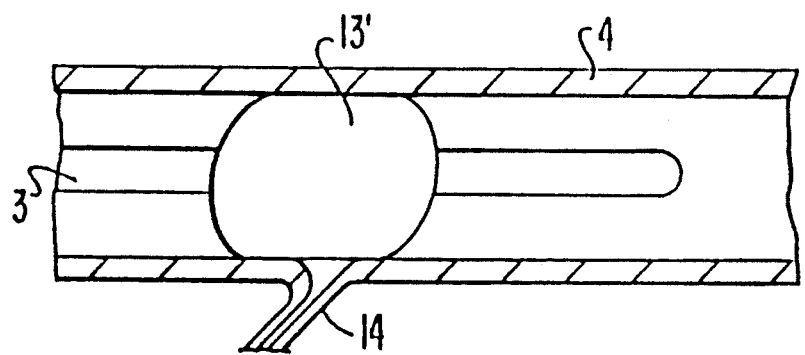
FIG. 7 is a side view similar to FIG. 1 showing a modified form of one component of a device for performing treatments according to the invention.

According to a further feature of the invention, catheter 3 may be provided with a balloon 13' which, upon inflation, assumes an oblong configuration, or is elongated in the longitudinal direction, as shown in FIG. 7. Such a balloon, which can be fabricated according to principles known in the balloon fabrication art, has an enhanced capability of blocking blood vessel side branches immediately adjacent the treatment site. If balloon 13' is provided, it may be necessary to place openings 28 and 32 at a greater distance from distal end 5 of catheter 2.

Another characteristic of the embodiment of FIG. 7 is that balloon 13' is configured to expand symmetrically around catheter 3. This permits balloon 13' to effectively block side branches at any location around the circumference of vessel 4.

While a preferred embodiment of a device according to the invention has been described and illustrated, it will be appreciated that various rearrangements of the component parts can be made without departing from the spirit and concept of the invention. Thus, as already mentioned, balloon 13 or 13' could be carried by infusion catheter 2. Alternatively, catheter 2 could carry a single balloon at the location of balloon 13, instead of at the location of balloon 12, particularly if, for any reason, it is desirable or necessary to insert catheter 3 from the direction opposite to that of catheter 2.

A treatment procedure according to the invention could further include introduction of an observation device to the treatment site.

As an alternative to the embodiments described above, embodiments of the invention may include but a single eccentric balloon, preferably mounted on infusion catheter 2. This arrangement may prove preferable for dealing with certain anatomical conditions encountered in the circulatory system. Depending on the conditions existing at the treatment site, relating to the actual blood flow pattern and the nature of the obstructions in the vicinity of the treatment site, the single balloon may be either at the distal location of balloon 12 or at the proximal location of balloon 13. Such an alternative arrangement would be utilized in situations where it is still possible to satisfy the goal of maintaining the desired quantity of treatment agent and the desired proportion of blood at the treatment site by appropriate control of the treatment agent delivery rate and the suction rate, while substantially preventing any significant flow of the treatment agent away from the treatment site and through the remainder of the circulatory system.

Treatments according to the invention may also be performed with a single catheter carrying one or two balloons, each of which may be eccentric or concentric to the catheter when expanded, the catheter having one inflation lumen for each balloon, a blood bypass flow lumen, and a treatment agent delivery lumen which also serves for the withdrawal of fluid samples for purposes of analysis and for the withdrawal of remaining treatment agent at the completion of the predetermined treatment period. By way of example, catheter 2 of FIGS. 1-3 could be used alone, with or without a second balloon.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for performing a therapeutic treatment on a section of a wall of a body passage, comprising:
    isolating a portion of the body passage which encloses the section from the remainder of the body passage;
    introducing into the isolated portion of the body passage a liquid medium containing a treatment agent;
    maintaining the treatment agent in the isolated portion for a predetermined time period;
    during said step of maintaining, periodically withdrawing a sample of the liquid medium from the isolated portion of the body passage, analyzing the sample to determine the proportion of treatment agent present in the liquid medium in the isolated portion and modifying the liquid medium in the isolated portion on the basis of the analysis to establish a desired proportion of the treatment agent in the liquid medium in the isolated portion.

2. A method as defined in claim 1 wherein the body passage is a blood vessel.

3. A method as defined in claim 2 wherein the liquid medium comprises blood.

4. A method as defined in claim 3 wherein the treatment agent comprises genetically altered cells.

5. A method as defined in claim 3 wherein said step of modifying comprises adding a quantity of treatment agent determined by the result of said analyzing step.

6. A method as defined in claim 2 wherein the predetermined time period is 30-60 minutes.

7. A method as defined in claim 1 wherein the liquid medium comprises a saline solution.

* * * * *